United States Patent
Yokoi et al.

(10) Patent No.: US 12,048,672 B2
(45) Date of Patent: Jul. 30, 2024

(54) PACKAGED MEDICINE

(71) Applicant: Otsuka Pharmaceutical Co., Ltd., Tokyo (JP)

(72) Inventors: Kazuma Yokoi, Osaka (JP); Kenzo Kashihara, Osaka (JP); Kenta Yamamoto, Osaka (JP); Takahiro Sonoki, Osaka (JP); Shohei Yamada, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1009 days.

(21) Appl. No.: 16/611,650

(22) PCT Filed: May 1, 2018

(86) PCT No.: PCT/JP2018/017426
§ 371 (c)(1),
(2) Date: Nov. 7, 2019

(87) PCT Pub. No.: WO2018/207681
PCT Pub. Date: Nov. 15, 2018

(65) Prior Publication Data
US 2020/0093700 A1 Mar. 26, 2020

(30) Foreign Application Priority Data

May 9, 2017 (WO) .................. PCT/JP2017/017537

(51) Int. Cl.
*A61J 3/02* (2006.01)
*A61J 1/00* (2023.01)
*A61J 3/07* (2006.01)
*A61J 3/10* (2006.01)

(52) U.S. Cl.
CPC . *A61J 3/07* (2013.01); *A61J 1/00* (2013.01); *A61J 3/10* (2013.01)

(58) Field of Classification Search
CPC ...... A61K 9/48; A61K 9/4808; A61K 9/4833; A61K 9/4883; A61K 9/50; A61B 5/0002; A61B 5/0004; A61B 5/0015; A61J 3/02
See application file for complete search history.

(56) References Cited

U.S. PATENT DOCUMENTS

| | | | | |
|---|---|---|---|---|
| 6,303,143 B1 * | 10/2001 | Chrai | ......... | B65B 1/04 424/464 |
| 6,705,467 B1 * | 3/2004 | Kancsar | ......... | B65D 83/0463 206/539 |
| 8,836,513 B2 | 9/2014 | Hafezi et al. | | |
| 2006/0127473 A1 * | 6/2006 | Nichols | ......... | A61P 27/16 514/649 |
| 2012/0062379 A1 | 3/2012 | Hafezi et al. | | |
| 2013/0129869 A1 | 5/2013 | Hafezi et al. | | |
| 2016/0136916 A1 | 5/2016 | Inaka | | |
| 2017/0000180 A1 * | 1/2017 | Arne | ......... | A23L 29/284 |

FOREIGN PATENT DOCUMENTS

| | | | | |
|---|---|---|---|---|
| CN | 101534707 A | 9/2009 | | |
| JP | H10-189238 A | 7/1998 | | |
| JP | H11180468 A | 7/1999 | | |
| JP | 2003-335380 A | 11/2003 | | |
| JP | 2008010711 A | 1/2008 | | |
| JP | 2009014469 A | 1/2009 | | |
| JP | 2014-138795 A | 7/2014 | | |
| JP | 2014-138954 A | 7/2014 | | |
| JP | 2014-525780 A | 10/2014 | | |
| JP | 2015-506913 A | 3/2015 | | |
| WO | WO-03055547 A1 * | 7/2003 | ........ | A61M 15/0043 |
| WO | WO-2006060458 A1 | 6/2006 | | |
| WO | WO-2008059415 A1 | 5/2008 | | |
| WO | WO-2008095183 A2 * | 8/2008 | ........... | A61B 5/0028 |
| WO | WO 2013/009788 | 1/2013 | | |
| WO | WO 2013/078411 | 5/2013 | | |
| WO | WO 2014/200046 A | 12/2014 | | |
| WO | WO 2015/112603 A1 | 7/2015 | | |

OTHER PUBLICATIONS

International Preliminary Report on Patentability for International Application No. PCT/JP2018/017426, mailed Nov. 21, 2019, 9 pages.
International Search Report for International Application No. PCT/JP2018/017426, mailed Jun. 5, 2018, 4 pages.
International Preliminary Report on Patentability for International Application No. PCT/JP2017/017537, mailed Nov. 21, 2019, 9 pages.
International Search Report for International Application No. PCT/JP2017/017537 dated Aug. 15, 2017, 5 pages.
Extended European Search Report for EP Application No. 18798510.6, mailed Nov. 5, 2020, 7 pages.
Examination Report in Australian Patent Application No. 2018264400, mailed Apr. 11, 2023, 5 pages.
Office Action in Korean Application No. 1020197035735, mailed Nov. 4, 2022, 7 pages.
Office Action in Korean Application No. 1020197035735, mailed Feb. 21, 2023, 5 pages.

* cited by examiner

*Primary Examiner* — Micah Paul Young

(57) ABSTRACT

Provided is packaged medicine capable of inhibiting deterioration of electrodes over a long period of time and reliably transmitting a signal after ingestion even when a long period of time has elapsed since production to ingestion. The packaged medicine includes a solid medicine including drug powder and a micro-device, a container provided with a solid medicine accommodating space accommodating the solid medicine therein, and inert gas encapsulated in the solid medicine accommodating space. The micro-device includes two electrodes with mutually different ionization tendencies and a transmitter operable to transmit a signal using electromotive force generated when the electrodes come in contact with electrolyte.

20 Claims, 6 Drawing Sheets

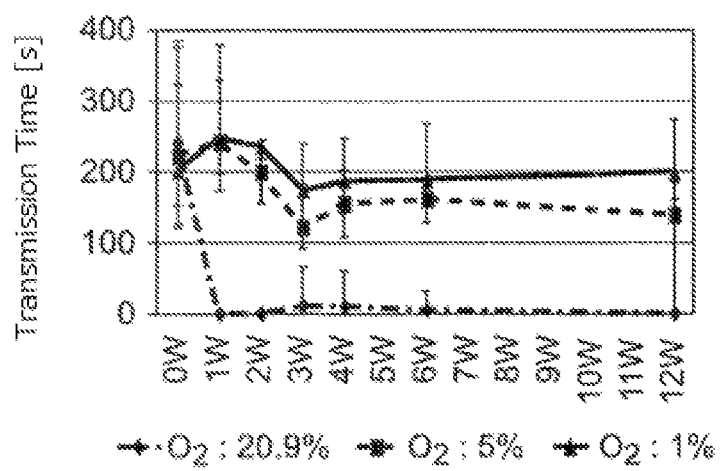
Fig. 4A (Experiment 1)
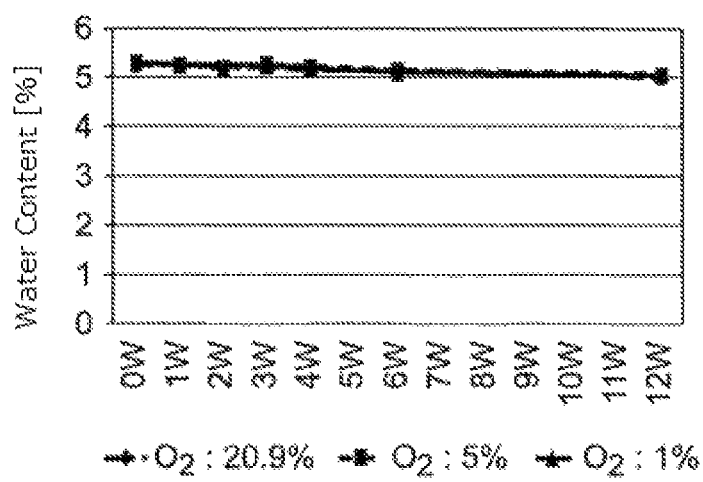
Fig. 4B (Experiment 1)

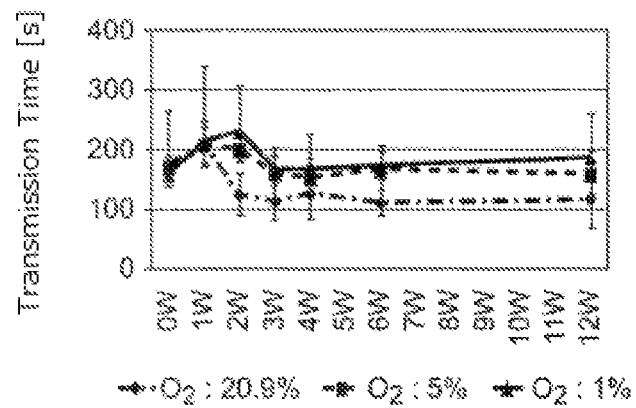
Fig. 5A (Experiment 2)
Lifetime: Signal Generation Time
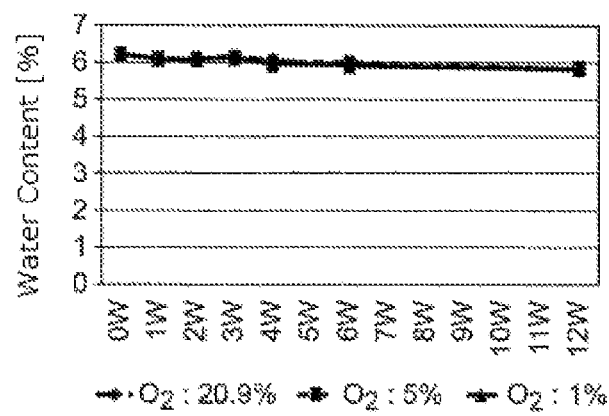
Fig. 5B (Experiment 2)
Tablet's Moisture

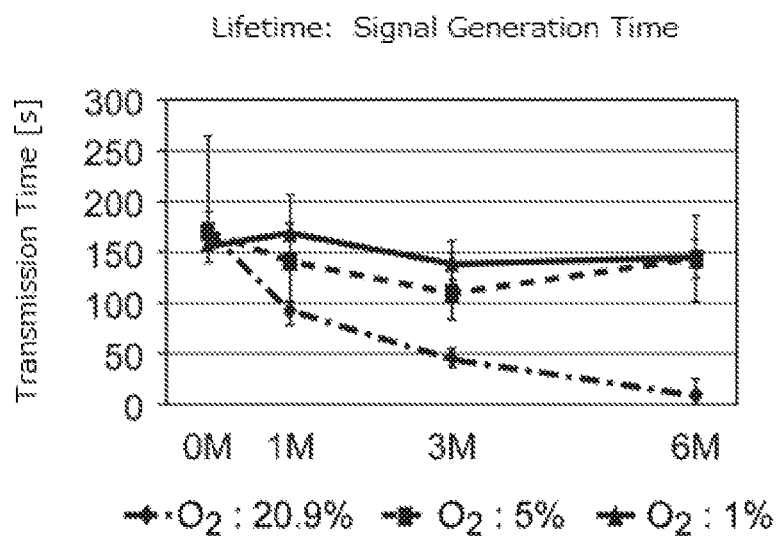
Fig. 6A (Experiment 3)
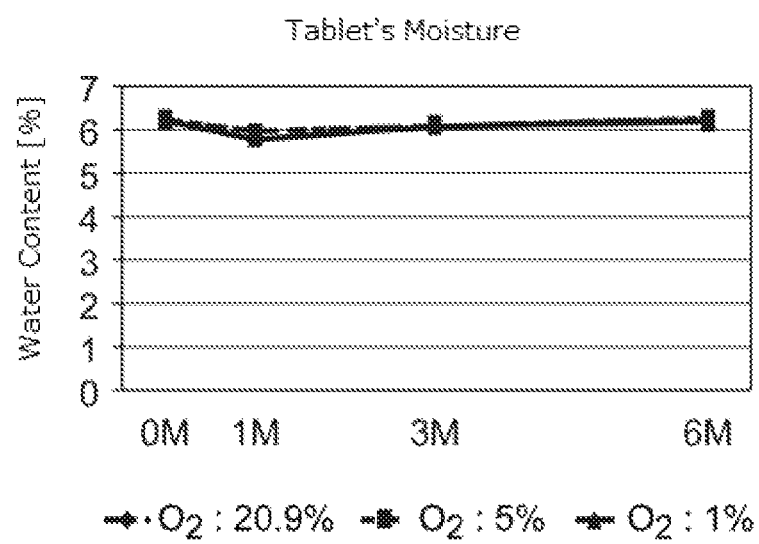
Fig. 6B (Experiment 3)

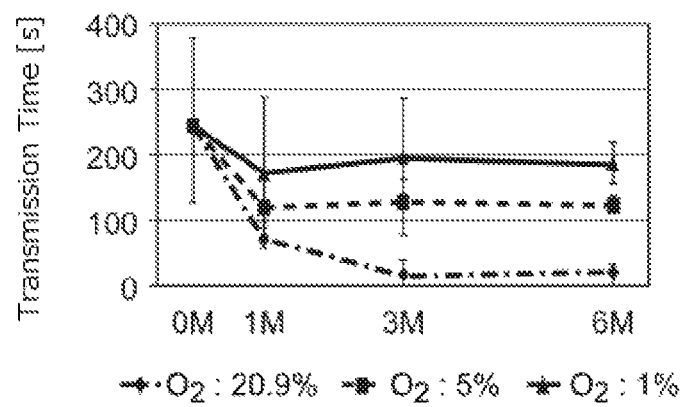
Fig. 7A (Experiment 4)
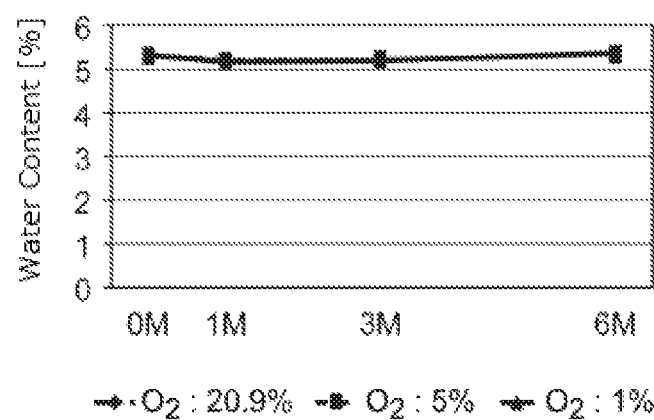
Fig. 7B (Experiment 4)

PACKAGED MEDICINE

CROSS-REFERENCE TO RELATED APPLICATION

This application is a U.S. National Stage Application under 35 U.S.C. § 371 of International Application No. PCT/JP2018/017426, filed May 1, 2018, entitled "PACKAGED MEDICINE", which is a continuation-in-part of and claims priority to and the benefit of International Application No. PCT/JP2017/017537, filed May 9, 2017, each of which is hereby incorporated herein by reference in its entirety.

TECHNICAL FIELD

The present invention relates to a packaged medicine in which a medicine (for example, tablet or capsule) including a micro-device is packaged in a container.

BACKGROUND ART

Patent Literatures (PTLs) 1 to 3 each disclose a tablet containing an embedded micro-device (IC-chip). The micro-chip embedded tablets can be manufactured by compressing, from above and below, a dose of powdered medicine containing a micro-device.

PTL 4 discloses, as one of the micro-device embedded tablets, a tablet with a transmitter which is designed to transmit a signal when the tablet is ingested into the body and then brought into contact with a conductive liquid (for example, gastric acid). In one embodiment disclosed in PTL 4, in order to produce a chemical battery, by using the conductive liquid in the body as an electrolyte, which generates electric power by the battery for signal transmitting, the micro-device has a pair of anode and cathode electrodes with mutually different ionization tendencies and a transmitter operable to transmit a signal using electric power generated between the electrodes. In this embodiment, for example, copper chloride is used for the anode electrode, and magnesium, sodium zinc, or lithium iron is used for the cathode electrode.

PRIOR ART DOCUMENTS

Patent Literatures

[PTL 1] JP 2014-138954 A
[PTL 2] JP 2014-138795 A
[PTL 3] JP 2014-200046 A
[PTL 4] JP 2014-525780 A

SUMMARY OF THE INVENTION

Disadvantageously, the anode electrode made of copper chloride tends to deteriorate with time. Conventionally, the deterioration of the anode has been thought to be caused by the contacts with other substances, in particular moisture. Then, to ensure the micro-device to fully exercise its ability, it was considered necessary to place the micro-device in a dry condition with the aid of desiccant agent.

Then, inventors of this application conducted an exhaustive study for providing an packaged medicine capable of protecting its electrode from being deteriorated over a long period of time and reliably transmitting signal when ingested irrespective of the time from production to ingestion, which shows that, once placed in the atmosphere, the anode electrode is susceptible to deterioration, in particular, by the contact with oxygen and moisture contained in the atmosphere, namely, that copper chloride (CuCl) forming the anode electrode of the micro-device contacts oxygen ($O_2$) and water ($H_2O$) in the ambient atmosphere to generate copper chloride hydroxide ($Cu_2(OH)_3Cl$) leading the deterioration of the anode electrode, which results in that the micro-device can fail to transmit an expected signal when ingested. Based upon the knowledge obtained by the study, the inventors found that isolating the tablet in a low-oxygen condition can protect the tablets from being making contact with oxygen and thereby prevent the tablet from being deteriorated even after a long period of time has elapsed from production, thereby leading to the present invention.

In order to achieve the object described above, a packaged medicine according to a present embodiment comprises:
  a solid medicine including drug powder and a micro-device;
  a container provided with a solid medicine accommodating space accommodating the solid medicine therein; and
  inert gas encapsulated in the solid medicine accommodating space,
  the micro-device including:
  a first electrode comprising a first material;
  a second electrode comprising a second material with a ionization tendency different from that of the first material; and
  a transmitter that transmits a signal using electromotive force generated between the first electrode and the second electrode when the first electrode and the second electrode are in contact with an electrolyte.

In another aspect of the present invention, the solid medicine is a tablet, and the micro-device is supported by the tablet.

In another aspect of the present invention, the solid medicine has a capsule, and the drug powder and a micro-device are accommodated in the capsule.

In another aspect of the present invention, the solid medicine has a capsule, the drug powder is accommodated in the capsule, and the micro-device is held in the capsule.

In another aspect of the present invention, the inert gas is nitrogen gas.

In another aspect of the present invention, the container is a blister package, a pouch package, a jar package, or a bottle package.

In another aspect of the present invention, the first material is copper chloride.

In another aspect of the present invention, the second material is magnesium.

In another aspect of the present invention, the drug powder is drug powder of which quality does not deteriorate even when coming into contact with oxygen.

According to an embodiment of the present invention configured in this manner, since a tablet placed in an environment with a low concentration of oxygen is isolated from oxygen and inhibited from deteriorating, even when the tablet is ingested after a long period of time has elapsed since production, the tablet can transmit a signal in a stable manner by entering a body and coming into contact with a body fluid (gastric acid).

BRIEF DESCRIPTION OF THE DRAWINGS

FIG. 4 is a graph showing a result of Experiment 1.

FIG. 5 is a graph showing a result of Experiment 2.

FIG. 6 is a graph showing a result of Experiment 3.

FIG. 7 is a graph showing a result of Experiment 4.

EMBODIMENTS OF THE INVENTION

Hereinafter, embodiments of packaged medicine according to the present invention will be described with reference to the accompanying drawings.

Figure 1:
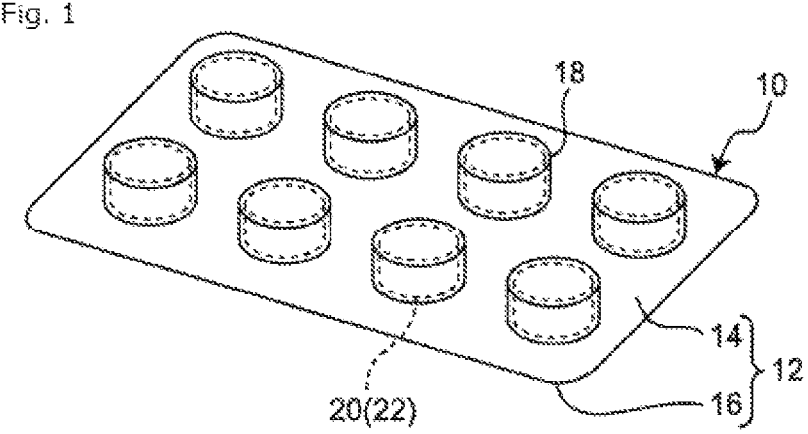
FIG. 1 is a perspective view of packaged medicine according to an embodiment of the present invention.

FIG. 1 shows a packaged medicine 10 according to an embodiment of the present invention. The illustrated packaged medicine 10 has a blister package (container) 12 or a blister package sheet. For example, the blister package 12 is made by bonding a transparent plastic sheet 14 and an aluminum sheet 16 forming respective upper and lower layers of the packaged medicine. The upper layer transparent plastic sheet 14 includes a plurality of chambers for accommodating medicines (medicine accommodating chambers) 18 formed by, for example, vacuum molding, each of which has a configuration matching with the medicine to be accommodated. Bottom openings of the medicine accommodating chambers 18 are sealed by the lower aluminum sheet 16.

Each of the medicine accommodating chambers 18 of the blister package 12 accommodates a solid medicine 20. In this embodiment, the solid medicine 20 is a tablet 22. Although the size of the tablet 22 is not limited, in consideration of ease of ingestion, the maximum size of the medicine is preferably 5 to 12 mm and, more favorably 7 to 8 mm.

Air in medicine accommodating chambers 18 is replaced during the production of the packaged medicine so that the tablet 22 is placed in an environment with a low concentration of oxygen. Although a replacement rate of inert gas does not need to be 100%, a proportion of oxygen remaining in the medicine accommodating chamber 18 is favorably as low as possible. Preferably, nitrogen is used for the inert gas, other inert gases may be employed instead.

A method for replacing the air in the medicine accommodating chamber 18 of the blister package 12 with inert gas is well known in JP 2011-213351 A, for example.

Figure 2:
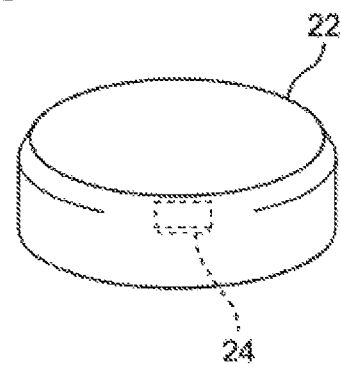
FIG. 2 is a perspective view of a tablet included in the packaged medicine shown in FIG. 1.

As shown in FIG. 2, the tablet 22 holds a micro-device (a micro-chip) 24. The maximum size of the micro-device 24 is 1 mm or less, more preferably several ten to several hundred micrometers.

In this embodiment, the micro-device 24 is held inside the tablet 22. As described in PTL's 1 to 3, the tablet which internally holds a micro-device in this manner is formed by compressing drug powder and a micro-device arranged thereinside from above and below. The tablet 22 may be a tablet made of drug powder of which quality does not deteriorate due to the contact with oxygen. The "drug powder of which quality does not deteriorate" refers to drug powders of which a reduction in content is 5% or less, an increase in analogous substances is 1.0% or less, or a reduction in elution is 10% or less, during a storage period of 36 months at a temperature of 25° C. or 6 months at a temperature of 40° C.

The micro-device 24 may be attached to a surface of the tablet 22. In this embodiment, preferably the micro-device 24 is attached to the surface of the tablet using an appropriate edible adhesive (for example, a starch glue).

Figure 3:
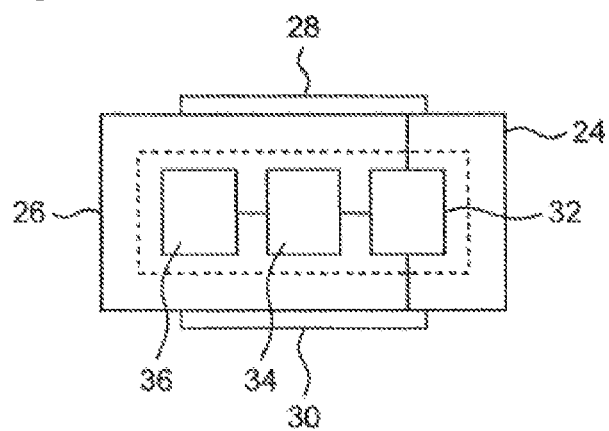
FIG. 3 is a circuit block diagram of a micro-device mounted in the tablet shown in FIG. 2.

As shown in FIG. 3, the micro-device 24 is made of a semiconductor integrated circuit substrate (silicon substrate) 26 with anode and cathode electrodes 28 and 30 mounted on the surface of the substrate. For example, the substrate 26 is manufactured using known semiconductor manufacturing techniques, and the anode and cathode electrodes 28 and 30 are produced using known film forming techniques. In this embodiment, copper chloride is used for the anode electrode 28 and magnesium is used for the cathode electrode 30.

Various circuits are formed on the substrate of the micro-device 24. For example, the micro-device 24 according to this embodiment a power supply unit (a power supply circuit) 32, a control unit (a control circuit) 34, and a transmitter (a transmitting circuit) 36. The power supply unit 32 is configured to be directly or indirectly connected to the anode and cathode electrodes 28 and 30, such that, when the micro-device 24 comes into contact with a conductive body fluid (for example, gastric acid), the power unit 32 cooperates with the anode and cathode electrodes 28 and 30 to form a chemical cell, which supplies electric power to other circuits. The control unit 34 is configured to receive the electric power supplied from the power supply unit 32 and transmit a signal to the transmitter 36. The transmitter 36 is configured to receive the electric power from the power supply unit 32 and transmit a signal in response to a signal from the control unit 34.

According to the packaged medicine 10 so constructed, the tablets 22 are accommodated in the medicine accommodating chambers 18 substantially filled with inert gas and are isolated from moisture and oxygen. Therefore, even when a long period of time elapses since production, no copper chloride hydroxide portion will be generated on the surface of electrodes of the micro-device 24, in particular, the anode electrode made of copper chloride. Also, when the tablet 22 is ingested into the body of a patient and then comes into contact with gastric acid, the anode electrode 28 and the cathode electrode 30 forms a chemical cell together with the gastric acid to generate electromotive force. The generated electric power is supplied from the power supply unit 32 to the control unit 34 and the transmitter 36. The transmitter 36 transmits a signal in response to a signal from the control unit 34. The transmitted signal is received by a patient's dedicated receiver or computer capable of receiving the signal (for example, a smartphone) installed with a dedicated software or application, recording the administration of the tablets.

EXPERIMENTS

The micro-devices were placed in different environments, and lifetimes (signal generation times) of the micro-devices were measured.

Experiment 1

Prepared were blister packages having a pair of opposite aluminum cover sheets and micro-device embedded tablets (A) disposed between the cover sheets. The blister packages were placed in experimental environments at a temperature of 60° C. with oxygen concentration of 20.9%, 5%, and 1%. After the elapse of zero week (0 W) (i.e., immediately after the placement in the experimental environment), 1 week (1 W), 2 weeks (2 W), 3 weeks (3 W), 4 weeks (4 W), 6 weeks (6 W), and 12 weeks (12 W), the tablets were taken out of respective experimental environments. The tablets were then brought into contact with an experimental solution to measure signal transmission times. Also, a water content (%) of the tablet [=(mass of moisture included in tablet/mass of medicine)×100] was measured at respective elapsed times. The experimental results are indicated in FIGS. 4A and 4B. In FIG. 4A, a vertical axis represents transmission time and a horizontal axis represents elapsed time. In FIG. 4B, a vertical axis represents water content and a horizontal axis represents measurement time points.

Experiment 2

Blister packages accommodating tablets B were prepared. Other experimental conditions were the same as those of Experiment 1. The experimental results are indicated in FIGS. 5A and 5B.

Experiments 3 and 4

Two types of double-sided aluminum blister packages with micro-device embedded tablets (A) and (B), respectively, were prepared. The blister packages were placed in experimental environments at a temperature of 40° C. with oxygen concentration of 20.9%, 5%, and 1%. After the elapse of zero week (0 W) (i.e., immediately after the placement in the experimental environment), 1 month (1 M), 3 months (3 M), and 6 months (6 M), the tablets were taken out of respective experimental environments. The tablets were then brought into contact with the experimental solution to measure signal transmission times. The results of experiments 3 and 4 for tablets (A) and (B), respectively, are indicated in FIGS. 6A and 6B and FIGS. 7A and 7B.

FIGS. 4B, 5B, 6B, and 7B show that the oxygen concentration in the package does not affect the amount of moisture included in a tablet. Also, FIGS. 4A, 5A, 6A, and 7A show that the performance of micro-device does not significantly decrease in the environments with low oxygen concentration (5% and 1%), but it decreases to a large extent during early stages (up until 1 W or 2 W) in the environment with high oxygen concentration (20.9%).

As described above, the experiments prove that the oxygen concentration in the environment significantly affects the deterioration of performance of the micro-device. Therefore, according to the embodiment of the present invention described above, tablets placed in the environment with a lower concentration of oxygen for a long time from production to ingestion can transmit a signal in a stable manner by the contact with the fluid in the body.

Figure 8:
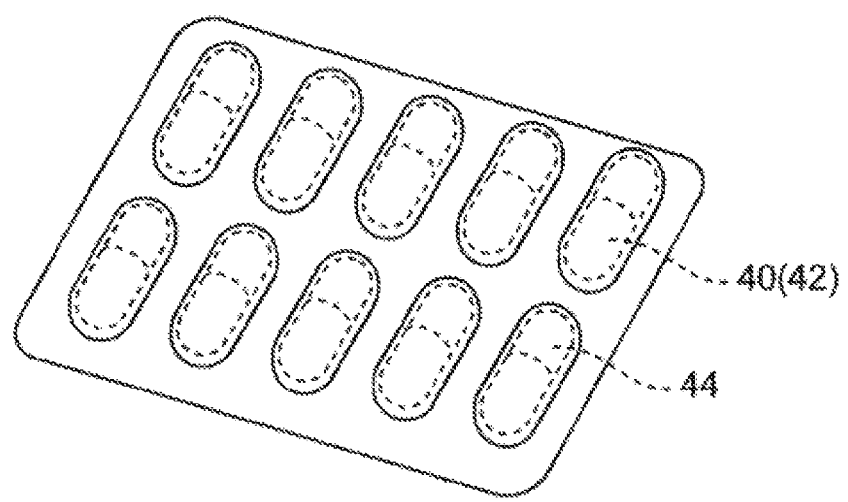
FIG. 8 is a perspective view of a packaged medicine according to another embodiment.

Although discussions have been made to the specific embodiment in which the solid medicines 40 in the packaged medicine are tablets, they may be capsules 42 shown in FIG. 8. In this embodiment, the micro-device may be loosely packed together with powdered medicine in a container 44 of the capsule.

Alternatively, the micro-device may be fixed on an inner or outer surface of the container 44. In this embodiment, preferably each electrode, in particular the anode electrode made of copper chloride susceptible to deterioration, is bonded and protected so that it does not make direct contacts with air.

Although in the previous embodiment the container of the packaged medicine is made of blister package having top and bottom aluminum sheets, it may be a laminated container made by bonding top plastic sheet and bottom aluminum sheet together.

Further, the container for accommodating the solid medicines is not limited to the blister package and may be a pouch package, jar package, or bottle package.

REFERENCE SIGNS 10 packaged medicine
12 blister package
14 plastic sheet
16 aluminum sheet
18 medicine accommodating chamber (medicine accommodating space)
20 solid medicine
22 tablet
24 micro-device
26 substrate
28 anode electrode
30 cathode electrode
32 power supply unit
34 control unit
36 transmitter
40 solid medicine
42 capsule
44 container

The invention claimed is:
1. A packaged medicine, comprising:
a plurality of ingestible solid medicines, each ingestible solid medicine from the plurality of ingestible solid medicines including drug powder;
a plurality of micro-devices, each micro-device from the plurality of micro-devices held by an ingestible solid medicine from the plurality of ingestible solid medicines; and
a container comprising an upper sheet and a lower sheet, the upper sheet and the lower sheet being bonded to each other to form a plurality of solid medicine accommodating chambers, wherein each solid medicine accommodating chamber from the plurality of solid medicine accommodating chambers separately accommodates one of the plurality of ingestible solid medicines thereinside, and wherein a gas disposed within each solid medicine accommodating chamber from the plurality of solid medicine accommodating chambers is substantially inert gas,
each micro-device from the plurality of micro-devices including:
a first electrode comprising a first material;
a second electrode comprising a second material with an ionization tendency different from that of the first material; and
a transmitter that transmits a signal using electromotive force generated between the first electrode and the second electrode when the first electrode and the second electrode are in contact with an electrolyte,
wherein the drug powder is a drug powder of which quality does not deteriorate by contact with oxygen such that, during a storage period of 36 months at a temperature of 25° C. or 6 months at a temperature of 40° C., a reduction in content is 5% or less or an increase in analogous substances is 1.0% or less.
2. The packaged medicine according to claim 1, wherein each ingestible solid medicine from the plurality of ingestible solid medicines is a tablet.
3. The packaged medicine according to claim 1, wherein:
each ingestible solid medicine from the plurality of ingestible solid medicines has a capsule, and
the drug powder and each micro-device from the plurality of micro-devices are accommodated in the capsule of each ingestible solid medicine from the plurality of ingestible solid medicines.

4. The packaged medicine according to claim 1, wherein:
   each ingestible solid medicine from the plurality of ingestible solid medicines has a capsule,
   the drug powder is accommodated in the capsule of each ingestible solid medicine from the plurality of ingestible solid medicines, and
   each micro-device from the plurality of micro-devices is held in the capsule of each ingestible solid medicine from the plurality of ingestible solid medicines.

5. The packaged medicine according to claim 1, wherein the inert gas is nitrogen gas.

6. The packaged medicine according to claim 1, wherein the container is a blister package or a pouch package.

7. The packaged medicine according to claim 1, wherein the first material is copper chloride.

8. The packaged medicine according to claim 1, wherein the second material is magnesium.

9. The packaged medicine according to claim 1, wherein the upper sheet is a transparent plastic sheet, and the lower sheet is an aluminum sheet.

10. The packaged medicine according to claim 1, wherein the upper sheet and the lower sheet are both aluminum sheets.

11. The packaged medicine according to claim 1, wherein each micro-device from the plurality of micro-devices is held inside the ingestible solid medicine holding that micro-device.

12. The packaged medicine according to claim 1, wherein each micro-device from the plurality of micro-devices is attached to a surface of the ingestible solid medicine holding that micro-device.

13. The packaged medicine according to claim 1, wherein:
   each ingestible solid medicine from the plurality of ingestible solid medicines has a capsule, the drug powder is accommodated in the capsule of each ingestible solid medicine from the plurality of ingestible solid medicines, and
   each micro-device from the plurality of micro-devices is fixed on an inner or outer surface of the capsule of a respective capsule of each ingestible solid medicine from the plurality of ingestible solid medicines.

14. The packaged medicine according to claim 13, wherein:
   the first material of the first electrode is copper chloride and the second material of the second electrode is magnesium, and
   the first electrode is bonded on the inner or outer surface of the capsule.

15. The packaged medicine according to claim 13, wherein an oxygen concentration in each solid medicine accommodating chamber from the plurality of solid medicine accommodating chambers is equal to or less than 5%.

16. A packaged medicine, comprising:
   a plurality of ingestible solid medicines, each ingestible solid medicine from the plurality of ingestible solid medicines including drug powder;
   a plurality of micro-devices, each micro-device from the plurality of micro-devices held by an ingestible solid medicine from the plurality of ingestible solid medicines, each ingestible solid medicine from the plurality of ingestible solid medicines including a capsule, the drug powder being accommodated in the capsule of each ingestible solid medicine from the plurality of ingestible solid medicines, each micro-device from the plurality of micro-devices being fixed on an inner or outer surface of a respective capsule of each ingestible solid medicine from the plurality of ingestible solid medicines; and
   a container comprising an upper sheet and a lower sheet, the upper sheet and the lower sheet being bonded to each other to form a plurality of solid medicine accommodating chambers, wherein each solid medicine accommodating chamber from the plurality of solid medicine accommodating chambers separately accommodates one of the plurality of ingestible solid medicines there inside, and wherein a gas disposed within each solid medicine accommodating chamber from the plurality of solid medicine accommodating chambers is substantially inert gas, an oxygen concentration in each solid medicine accommodating chamber from the plurality of solid medicine accommodating chambers being equal to or less than 5%,
   each micro-device from the plurality of micro-devices including:
      a first electrode comprising a first material;
      a second electrode comprising a second material with an ionization tendency different from that of the first material; and
      a transmitter that transmits a signal using electromotive force generated between the first electrode and the second electrode when the first electrode and the second electrode are in contact with an electrolyte,
   wherein the drug powder is a drug powder of which quality does not deteriorate by contact with oxygen.

17. The packaged medicine according to claim 16, wherein the inert gas is nitrogen gas.

18. The packaged medicine according to claim 16, wherein the first material is copper chloride.

19. The packaged medicine according to claim 16, wherein the second material is magnesium.

20. The packaged medicine according to claim 16, wherein the first material is copper chloride, the second material is magnesium, and the first electrode is bonded on the inner or outer surface of the capsule.

* * * * *